(12) United States Patent
Richard et al.

(10) Patent No.: US 6,375,940 B1
(45) Date of Patent: *Apr. 23, 2002

(54) USE OF A SCREENING SILICONE FOR PROTECTING THE COLOR OF ARTIFICIALLY COLORED KERATIN FIBRES AGAINST THE EFFECTS OF UV RADIATION

(75) Inventors: Hervé Richard, Villepinte; Alain Lagrange, Coupvray; Claude Dubief, Le Chesnay; Damarys Braida-Valerio, Paris, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/951,048

(22) Filed: Oct. 15, 1997

(30) Foreign Application Priority Data

Oct. 15, 1996 (FR) .............................. 96 12564

(51) Int. Cl.⁷ ..................... A61K 70/13; A61K 70/06
(52) U.S. Cl. .................... 424/70.6; 424/70.6; 424/70.9; 424/70.11; 424/70.12; 424/70.121; 424/59; 424/401; 8/406
(58) Field of Search ........................ 424/401, 59, 70.12, 424/70.6, 70.9, 70.11, 70.121; 8/406

(56) References Cited

U.S. PATENT DOCUMENTS

| | | | |
|---|---|---|---|
| 5,061,479 A | 10/1991 | Grollier et al. | 424/47 |
| 5,089,250 A | 2/1992 | Forestier et al. | 424/43 |
| 5,145,662 A | 9/1992 | Forestier et al. | 424/45 |
| 5,223,249 A | 6/1993 | Forestier et al. | 424/59 |
| 5,270,426 A | 12/1993 | Sakuta et al. | 528/15 |
| 5,403,944 A * | 4/1995 | Frater et al. | 556/441 |
| 5,415,854 A | 5/1995 | Forestier et al. | 424/59 |
| 5,610,257 A | 3/1997 | Richard et al. | 528/15 |
| 6,120,757 A * | 9/2000 | Dubief et al. | 424/70.9 |

FOREIGN PATENT DOCUMENTS

| | | |
|---|---|---|
| EP | 0 335 777 | 10/1989 |
| EP | 0 383 655 | 8/1990 |
| EP | 0 389 337 | 9/1990 |
| EP | 0 708 108 | 4/1996 |
| EP | 0 709 080 | 5/1996 |
| EP | 0 711 779 | 5/1996 |
| EP | 0 742 003 | 11/1996 |
| FR | 2 642 967 | 8/1990 |
| FR | 2 642 968 | 8/1990 |
| FR | 2 657 351 | 7/1991 |
| WO | WO 92/20690 | 11/1992 |

OTHER PUBLICATIONS

English Derwent Abstract of EP 0 708 108.

English Derwent Abtract of EP 0 742 003.

* cited by examiner

Primary Examiner—Diana Dudash
Assistant Examiner—Shahnam Sharareh
(74) Attorney, Agent, or Firm—Finnegan, Henderson, Farabow, Garrett & Dunner, L.L.P.

(57) ABSTRACT

The use of an organosiloxane bearing at least one ultraviolet-absorbing group in, and for the preparation of, a cosmetic or dermatological composition as an agent for protecting the colour of artificially coloured keratin fibres against the effects of UV radiation, in particular solar radiation.

17 Claims, No Drawings

USE OF A SCREENING SILICONE FOR PROTECTING THE COLOR OF ARTIFICIALLY COLORED KERATIN FIBRES AGAINST THE EFFECTS OF UV RADIATION

The present application relates to the use of an organosiloxane bearing at least one ultraviolet-absorbing group in, and for the preparation of, a cosmetic or dermatological composition as an agent for protecting the colour of artificially coloured keratin fibres against the effects of UV radiation, in particular solar radiation.

It has been known for a long time that washing agents and light in particular have a tendency to attack the artificial colour of dyed hair. The hair colour thus obtained after a dyeing treatment gradually fades or turns to less attractive or desirable shades.

It has thus been found necessary to protect the colour of keratin fibres which have undergone a dyeing treatment, and in particular the colour of hair, and to substantially reduce the degradations associated with the action of external agents, in particular UV radiation and more particularly solar radiation.

The inventors have discovered, and this forms the subject of the invention, that screening silicones bearing ultraviolet-absorbing groups preserve, surprisingly, the colour of artificially coloured keratin fibres and in particular the hair, by substantially reducing the degradations associated with the action of UV radiation, in particular the action of solar radiation.

The subject of the invention is therefore the use of an organosiloxane bearing at least one ultraviolet-absorbing group in, and for the preparation of, a cosmetic or dermatological composition as an agent for protecting the colour of artificially coloured keratin fibres against the harmful effects of UV radiation, in particular solar radiation.

Other subjects will become apparent on reading the description and the examples which follow.

The organosiloxanes bearing ultraviolet-absorbing groups, which are used according to the invention, preferably contain in their molecule at least one unit of formula:

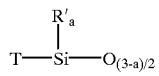
(I)

in which:
R' denotes a saturated or unsaturated $C_1$–$C_{30}$ hydrocarbon group, a $C_1$–$C_8$ halogenated hydrocarbon group, an aromatic hydrocarbon group or a trimethylsiloxy group;
a=1 or 2;
T=—E—U where E represents a saturated or unsaturated, linear or branched aliphatic divalent hydrocarbon radical having at least 2 carbon atoms and optionally containing one or more oxygen atoms, or alternatively an aromatic group, and U represents the residue of a molecule which screens ultraviolet radiation.

In addition to the units of formula (I), the polyorganosiloxane may contain units of formula (II) and/or units of formula (III):

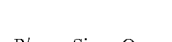
(II)

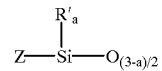
(III)

in which:
R' and a have the same meanings as in formula (I);
b=1,2 or 3;
Z=—O—U, U having the same meaning as in formula (I).

As hydrocarbon group, mention may be made of $C_1$–$C_{30}$ alkyl, $C_2$–$C_{30}$ alkenyl or cycloalkyl radicals or aromatic radicals such as phenyl or toluyl.

As halogenated hydrocarbon group, mention may be made of the 3,3,3-trifluoropropyl radical.

In the organopolysiloxanes in accordance with the invention, comprising units of formula (I) and optionally units of formula (II) and/or of formula (III), preferably, at least 40%, in numerical terms, of the radicals R' are methyl radicals. The total number of units (I), (II) and (III) is preferably less than or equal to 250 and ranges in particular from 2 to 50.

U preferably represents one of the following residues:
benzylidenecamphor optionally substituted on the benzene ring with hydroxyl or $C_1$–$C_8$ alkyl or alkoxy radicals;
di($C_1$–$C_8$)alkyl benzalmalonate optionally substituted on the benzene ring with hydroxyl or $C_1$–$C_8$ alkyl or alkoxy radicals;
2-(2'-hydroxyphenyl)benzotriazole optionally bearing, on one of the aromatic rings, $C_1$–$C_8$ alkyl or $C_2$–$C_8$ alkenyl, halogen, alkoxy, carboxyl, hydroxyl, amino or tetraalkylpiperidyl substituents;
dibenzoylmethane optionally bearing $C_1$–$C_8$ alkyl or alkoxy or hydroxyl radicals;
benzophenone optionally bearing $C_1$–$C_8$ alkyl or alkoxy or hydroxyl radicals;
benzoate substituted with hydroxyl, $C_1$–$C_6$ alkoxy, amino or mono- or di($C_1$–$C_6$ alkyl)amino radicals;
cinnamate optionally bearing hydroxyl, $C_1$–$C_6$ alkyl or alkoxy, amino or mono- or di($C_1$–$C_6$ alkyl)amino radicals;
bis- or tris(phenylacrylate) optionally substituted with hydroxyl or $C_1$–$C_4$ alkoxy radicals.

These organopolysiloxanes bearing ultraviolet-absorbing groups are described in particular in European patent applications Nos. 0,335,777, 0,305,059, 0,392,882, 0,392,883, 0,388,218, 0,350,314, 0,383,655, 0,389,337, 0,709,080 and 0,538,431, in International patent application WO 92/20690, in French patent applications Nos. 2,550,787 and 2,657,351 and in American patents U.S. Pat. Nos. 4,696,969, 4,554,369, 4,562,278, 3,513,184 and 4,859,759, the disclosures of which are specifically incorporated by reference herein.

Particularly preferred screening silicones of the invention are chosen from those containing a benzotriazole function, which correspond to the following formulae:

(1)

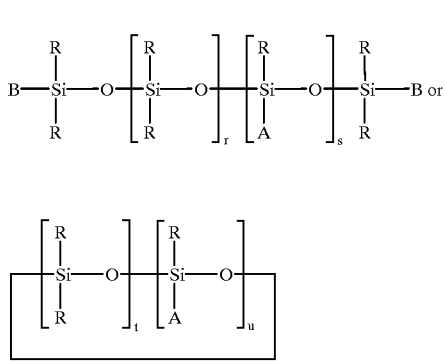

(2)

in which in formulae (1) and (2):
R, which may be identical or different, are chosen from $C_1$–$C_{10}$ alkyl, phenyl and 3,3,3-trifluoropropyl radicals, at least 80%, in numerical terms, of the radicals R being methyl,
B, which may be identical or different, are chosen from radicals R and the radical A,
r is an integer ranging from 0 to 50, and s is an integer ranging from 0 to 20, and if s=0, at least one of the two symbols B denotes A,
u is an integer ranging from 1 to 6, and t is an integer ranging from 0 to 10, it being understood that t+u is equal to or greater than 3,
and the symbol A denotes a monovalent radical linked directly to a silicon atom and corresponding to formula (3) below:

(3)

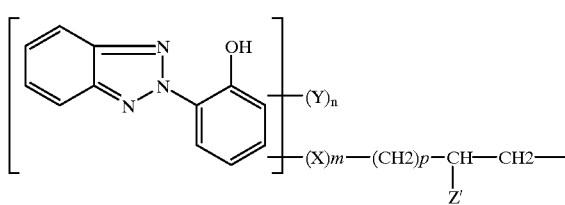

in which
Y, which may be identical or different, are chosen from $C_1$–$C_8$ alkyl radicals, halogens and $C_1$–$C_4$ alkoxy radicals, it being understood that, in the latter case, two adjacent Y groups of the same aromatic ring may together form an alkylidenedioxy group in which the alkylidene group contains from 1 to 2 carbon atoms,
X represents O or NH,
Z' represents hydrogen or a $C_1$–$C_4$ alkyl radical,
n is an integer ranging from 0 to 3,
m is 0 or 1,
p represents an integer ranging from 1 to 10.

As emerges from formula (3), given above, attachment of the chain unit —(X)$_m$—(CH2)$_p$—CH(Z')—CH$_2$— to the benzotriazole moiety, which thus ensures connection of the said benzotriazole moiety to the silicon atom of the silicon-containing chain, may, according to the present invention, take place in any of the available positions of the two aromatic rings of the benzotriazole:

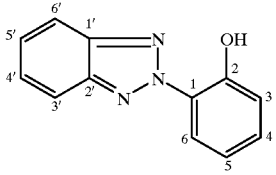

This attachment preferably takes place in position 3, 4, 5 (aromatic ring bearing the hydroxyl function) or 4' (benzene ring adjacent to the triazole ring) and, even more preferably, in position 3, 4 or 5. In a preferred embodiment of the invention, the attachment takes place in position 3.

Similarly, the substituent moiety or moieties Y may be attached in any of the other available positions on the benzotriazole. However, this attachment preferably takes place in position 3,4,4',5 and/or 6. In a preferred embodiment of the invention, attachment of the moiety Y takes place in position 5.

In the above formulae (1) and (2), the alkyl radicals may be linear or branched and chosen in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R according to the invention are methyl, ethyl, propyl, n-butyl, n-octyl and 2-ethyhexyl radicals. Even more preferably, the radicals R are all methyl radicals.

These screening silicones are described, along with the process for their synthesis, in application EP-A-0,392,883 and in application WO 94/06404, the disclosures of which are specifically incorporated by reference herein.

Among the compounds of formula (1) or (2) above, it is preferred to use those corresponding to formula (1), that is to say diorganosiloxanes with a short linear chain.

Among the compounds of formula (1) above, it is preferred to use those in which the radicals B are both radicals R.

Among the linear diorganosiloxanes falling within the scope of the present invention, random derivatives or derivatives with well-defined blocks having at least one and even more preferably all of the following characteristics:
B is a radical R,
R is alkyl and even more preferably is methyl,
r ranges from 0 to 15; s ranges from 1 to 10,
n is non-zero and is preferably equal to 1, and Y is then chosen from methyl, tert-butyl and $C_1$–$C_4$ alkoxy,
Z' is hydrogen or methyl,
m=0 or [m=1 and X=O],
p is equal to 1, are more particularly preferred.

One family of compounds which is particularly suitable for the invention is that defined by the general formula (4) below:

(4)

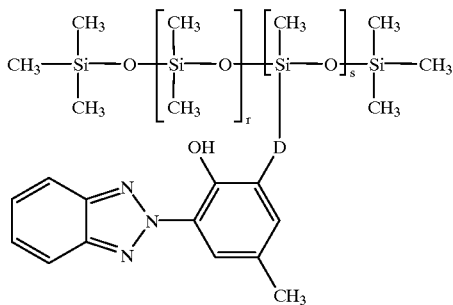

with

0<r<10,

1<s<10, and where D represents the divalent radical:

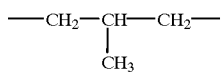

In a particularly preferred embodiment of the invention, the benzotriazole silicone is the compound (referred to hereinbelow as compound (c)) corresponding to the following formula:

compound (c)

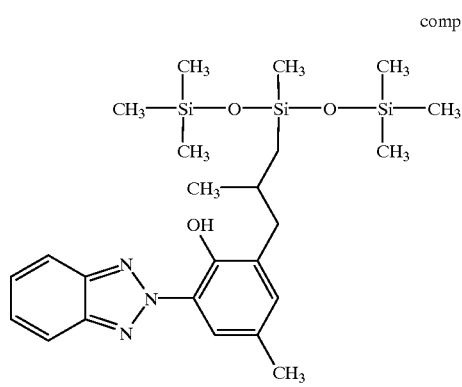

Another family of screening silicones which is particularly preferred comprises benzalmalonate silicones containing at least some units corresponding to one of the two formulae (5) and (6) below:

(5)

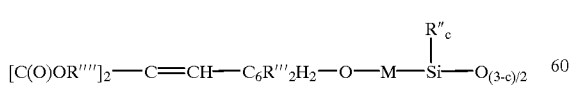

(6)

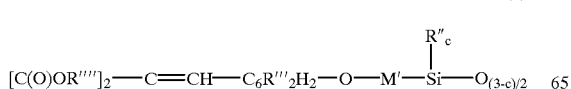

in which:

M denotes a group having the structure:

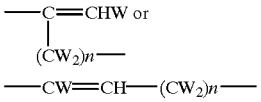

M' denotes a group having the structure:

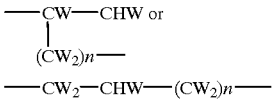

the other units of the silicone which are present having the structure:

(7)

$$Q_d\!-\!Si\!-\!O_{(4-d)/2}$$

where R", which may be identical or different, denote an aryl or $C_1$–$C_8$ alkyl radical; W, which may be identical or different, denote a hydrogen or a $C_1$–$C_5$ alkyl radical; R''', which may be identical or different, denote a hydrogen or a $C_1$–$C_5$ alkyl radical or a radical OW; R'''', which may be identical or different, denote denotes a $C_1$–$C_5$ alkyl group; Q, which may be identical or different, denote a hydrogen, a monovalent $C_1$–$C_8$ hydrocarbon radical or a halogenated hydrocarbon group; c is equal to 0, 1 or 2; d is equal to 0, 1, 2 or 3 and n ranges from 1 to 6; with the proviso that the group —M—O— or —M'—O— is connected to the aromatic ring in a meta or para position relative to the group:

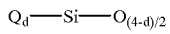

and with the proviso that the two groups R''' occupy the other remaining positions on the aromatic ring.

These screening silicones are described, along with processes for their preparation, in patent applications EP-A-0,392,882, EP-0,538,431, EP-A-0,709,080 and WO92/20690, the disclosures of which are specifically incorporated by reference herein.

In a particularly preferred embodiment of the invention, one family of compounds which is particularly desired is that defined by the benzalmalonate silicones chosen from:

(i) silicones corresponding to formula (8) below:

(8)

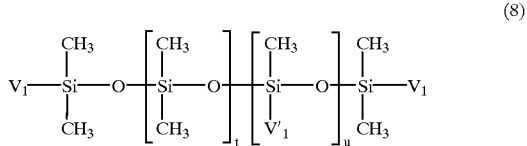

in which:

V'$_1$ denotes a group having the structure:

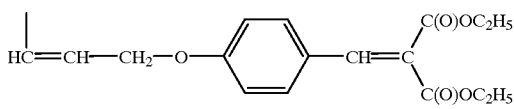

V$_1$, which may be identical or different, denote CH$_3$ or V'$_1$;

(ii) silicones corresponding to formula (9) below:

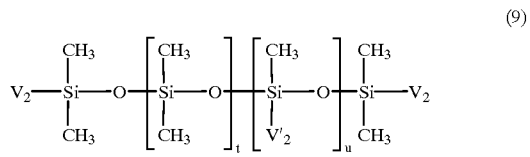

(9)

in which:

V'$_2$ denotes a group having the structure:

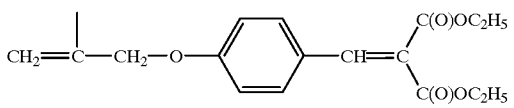

V$_2$, which may be identical or different, denote CH$_3$ or V'$_2$;

(iii) mixtures thereof;
with 0<t<100 and 0<u<20, with the proviso that:
when V$_1$=V'$_1$ and/or V$_2$=V'$_2$ then u=0; and
when V$_1$=CH$_3$ and/or V$_2$=CH$_3$ then 1<u<20.

The screening organosiloxanes of the invention are preferably used in amounts equal to at least 0.01% by weight and generally ranging from 0.1 to 20% by weight and more particularly from 0.1 to 10% by weight relative to the weight of the composition intended to be applied to the naturally or artificially coloured keratin fibres.

The compositions intended to be applied to the dyed keratin fibres in accordance with the invention may be in the form of an oily, alcoholic or aqueous-alcoholic lotion, in the form of an emulsion or in the form of an aqueous or aqueous-alcoholic dispersion.

When the compositions constitute oily lotions, they contain, besides the organosiloxane bearing an ultraviolet-absorbing group, mineral, plant, animal or synthetic oils and more particularly isoparaffins or silicone oils with a linear or cyclic structure, such as polyalkylsiloxanes, polyarylsiloxanes, polyalkylarlysiloxanes or polyorganosiloxanes modified with non-chromophoric organofunctional groups.

The oily compositions may also contain waxes, resins or silicone gums together with the oils defined above.

The alcoholic lotions contain, besides the organosiloxane bearing an ultraviolet-absorbing group, for example a lower alcohol containing 1 to 4 carbon atoms and preferably ethanol or isopropanol, or alternatively other alcohols such as alkylene glycols or glycol ethers.

When the compositions of the invention are emulsions, the fatty phase of the emulsions comprises either solely the screening organosiloxane or a mixture of the latter with other oils or waxes as defined above. The other phase of the emulsions comprises an aqueous medium.

The nonionic emulsions of the invention contain a nonionic emulsifier chosen, for example, from polyoxyethylenated fatty alcohols, polyoxyethylenated fatty acids, optionally polyoxyethylenated sorbitan esters, polyoxyethylenated or polyglycerolated alkylphenols, polyoxyethylenated or polyglycerolated fatty amides, and polyglycerolated fatty alcohols and alpha-diols; the number of moles of ethylene oxide preferably ranges from 2 to 50, and the number of glycerol groups preferably ranges from 2 to 30.

The cationic emulsions of the invention contain a cationic emulsifier chosen, for example, from quaternary ammonium halides such as di(C$_{10}$–C$_{30}$)alkyldimethylammonium halide, (C$_{10}$–C$_{30}$)alkyltrimethylammonium halide or (C$_{10}$–C$_{30}$)alkylbenzyldimethylammonium halide, and polyoxyethylenated quaternary ammonium salts containing from 2 to 30 mol of ethylene oxide. Distearyidimethyl-ammonium chloride and behenyltrimethylammonium chloride are more particularly used.

When the compositions of the invention are dispersions, they generally contain water and optionally an alcohol such as those mentioned above, a dispersion agent or an agent for suspending the screening silicone in water. Ammonium acrylate/acrylamide copolymers and crosslinked acrylic acid polymers may be mentioned, for example, as dispersion agents.

The compositions in accordance with the invention may also contain any other additive usually applied to keratin fibres and in particular the hair, such as, for example, dyes, surfactants, polymers, thickeners, conditioners, fragrances, preserving agents and softeners, as well as other screening agents, The compositions in accordance with the invention may also be in the form of a spray or may be pressurized in aerosol devices.

The compositions of the invention intended to be applied to artificially coloured keratin fibres, and in particular human hair, are rinse-out products applied after dyeing, such as shampoos or conditioners, or alternatively leave-in products applied after dyeing, such as styling lotions, gels or foams, aerosol lacquers or sprays.

Artificially coloured keratin fibres, and in particular hair, are dyed using dyes that are used conventionally for the hair, such as oxidation dye precursors, by a dyeing process using an oxidizer such as aqueous hydrogen peroxide solution or air or alternatively by direct dyeing. Another possibility is to dye the keratin fibres in the presence of the screening organosiloxane. Another possibility is to apply a composition according to the invention based on the screening organosiloxane before dyeing the keratin fibres.

The subject of the present invention is also a cosmetic treatment process intended to protect the colour of dyed hair against the harmful effects of UV radiation, and in particular solar radiation, comprising the step of applying, before or after dyeing the hair, an effective amount of a cosmetic or dermatological composition containing at least one organ-opolysiloxane compound as defined above.

The examples which follow serve to illustrate the invention without, however, being limiting in nature.

FORMULATION EXAMPLES

EXAMPLE 1

Conditioner for Protecting Hair Colour

| | |
|---|---|
| Organosiloxane containing benzotriazole functionality, of formula (4), compound (c), referred to above | 1 g |
| Cyclopentadimethylsiloxane sold under the name DC245 by Dow Corning | 15 g |

-continued

| | |
|---|---|
| Cyclotetradimethylsiloxane sold under the name DC244 by Dow Corning | 15 g |
| α,Ω-dihydroxylated polydimethylsiloxane/volatile silicone, sold under the name Q2 1401 by Dow Corning | 20 g |
| Ethanol | 5 g |
| Water | qs 100 g |

EXAMPLE 2

Gel Hair Conditioner

| | |
|---|---|
| Organosiloxane containing benzotriazole functionality, of formula (4), compound (c), referred to above | 6 g |
| α,Ω-dihydroxylated polydimethylsiloxane/volatile silicone, sold under the name Q2 1401 by Dow Corning | 20 g |
| Acrylamide/2-acrylamido-2-methylpropanesulphonic acid crosslinked copolymer sold under the name Sepigel 305 by Seppic | 1 g AM |
| Water | qs 100 g |

This gel makes it possible to reduce substantially the degradation of the hair colour associated with the action of external agents, in particular light.

EXAMPLE 3

Gel Hair Conditioner

| | | |
|---|---|---|
| Organosiloxane containing benzotriazole functionality, of formula (4), compound (c), referred to above | 6 | g |
| Polydimethylsiloxane sold under the name Silbione V 500000 by Rhône-Poulenc | 10 | g |
| Acrylamide/2-acrylamido-2-methylpropanesulphonic acid crosslinked copolymer sold under the name Sepigel 305 by Seppic | 1 | g AM |
| Water | qs 100 | g |

This gel makes it possible to reduce substantially the degradation of the hair colour associated with the action of external agents, in particular light.

EXAMPLE 4

Shampoo for Protecting the Hair Colour

| | |
|---|---|
| Organosiloxane containing benzalmalonate functionality of formula (9), wherein $V_2$ is methyl, t is about 60, and u is about 4 | 1 g |
| Sodium lauryl ether sulphate containing 2.2 mol of ethylene oxide | 15 g AM |
| Cocoylbetaine | 2.4 g AM |
| Ethylene glycol distearate | 2.5 g |
| Coconut acid monoisopropanolamide | 2.5 g |
| Water | qs 100 g |

This shampoo has good washing properties and makes it possible, after application and rinsing, to substantially reduce the degradation of the hair colour associated with the action of external agents, in particular light.

Comparative Example

Oxidation dyeing is carried out on a first series of 1.2 g locks of slightly sensitized hair, leading to an "ashen dark-blond" shade.

Oxidation dyeing is carried out on a second series of 1.2 g locks of slightly sensitized hair, leading to a "mahogany golden dark-blond" shade.

The locks thus dyed are then treated with composition A, B or C according to the procedure indicated below:

Composition A (invention):

| | |
|---|---|
| Organosiloxane containing benzotriazole functionality of formula (4), compound (c), referred to above | 1% by weight |
| Absolute ethanol | qs 100% by weight |

Composition B (invention):

| | |
|---|---|
| Organosiloxane containing benzalmalonate functionality of formula(9), wherein $V_2$ is methyl, t is about 60, and u is about 4 | 1% by weight |
| Absolute ethanol | qs 100% by weight |

Composition C (control):

| | |
|---|---|
| Absolute ethanol | 100% by weight |

Procedure:

Each dyed lock is immersed for 10 seconds in 400 ml of deionized water. They are then blotted between 2 sheets of paper (twice). Each dyed lock is then treated with 1 ml of test composition A, B or C for 10 min. After squeezing out the liquid between two fingers, the locks are dried under a hood for 30 min at 65° C.

The locks thus treated then undergo a test of light-fastness (Xenotest).

To do this, the locks of dyed hair were fixed to a support (cardboard or plastic). These supports were arranged on sample holders which rotate around a Xenon lamp for a period of 60 hours under a relative humidity level of 25±5% and at a temperature of 42.5±2.5° C.

The colours of the locks were evaluated in the L a b system using a Minolta CM 2002 calorimeter.

In this system, the following are measured for each lock:

the colour of the lock obtained after treatment with composition A, B or C and before the light-fastness test, and the colour of the lock obtained after the light-fastness test.

In this system, L indicates the lightness. The higher the value of L, the lighter the shade. Conversely, the lower the value of L, the darker the shade.

The shade and the saturation are expressed by a and b. a and b indicate two shade axes, a indicating the red/green axis and b the yellow/blue axis. Values close to zero for a or b correspond to grey shades.

The difference in colour of each lock before and after the light-fastness test reflects the degradation of the coloration due to the action of light, and was calculated by applying the following equation:

$$\Delta E = \sqrt{(L-L_0)^2 + (a-a_0)^2 + (b-b_0)^2}$$

In this formula, $\Delta E$ represents the difference in colour between two locks, L, a and b respectively represent the lightness, the shade and the saturation after the test and $L_0$, $a_0$ and $b_0$ respectively represent the lightness, the shade and the saturation before the test.

The test results are given in Tables 1 and 11 below:

TABLE I

| Composition | Colour before the test on hair dyed ashen dark-blond | | | Colour after the test on hair dyed ashen dark-blond | | | Degradation of the colour $\Delta E$ on hair dyed ashen dark-blond |
|---|---|---|---|---|---|---|---|
| | L | a | b | L | a | b | |
| A (invention) | 22.16 | 2.39 | 4 | 28.54 | 4.06 | 10.84 | 9.50 |
| B (invention) | 22.6 | 2.35 | 3.97 | 21.91 | 3.77 | 11.19 | 9.12 |
| C (control) | 22.58 | 2.23 | 3.6 | 30.07 | 4.52 | 13.07 | 12.29 |

It is observed that compositions A and B according to the invention containing a screening silicone reduce the degradation of the colour of artificially coloured locks by 23 and 26% respectively, after exposure to light for 60 hours, relative to composition C which lacks screening silicone.

TABLE II

| Composition | Colour before the test on hair dyed ashen dark-blond | | | Colour after the test on hair dyed ashen dark-blond | | | Degradation of the colour $\Delta E$ on hair dyed ashen dark-blond |
|---|---|---|---|---|---|---|---|
| | L | a | b | L | a | b | |
| A (invention) | 33.79 | 10.04 | 16.55 | 43.17 | 8.1 | 21.81 | 10.93 |
| B (invention) | 33.75 | 10.21 | 16.95 | 41.67 | 8.26 | 21.94 | 9.56 |
| C (control) | 34.59 | 10 | 16.82 | 45.96 | 7.98 | 23.54 | 13.36 |

It is observed that compositions A and B according to the invention containing a screening silicone reduce the degradation of the colour of artificially coloured locks by 18 and 28% respectively, after exposure to light for 60 hours, relative to composition C which lacks screening silicone.

We claim:

1. A process for protecting the color of artificially colored keratin fibers against the effects of UV radiation, comprising dyeing said artificially colored keratin fibers according to an oxidation dyeing process using at least one oxidation dye precursor, at least one oxidation agent, and an effective amount of at least one organosiloxane containing at least one unit of formula (I) below:

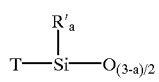
(I)

wherein:
R', which may be identical or different, is chosen from saturated and unsaturated $C_1$–$C_{30}$ hydrocarbon groups, $C_1$–$C_8$ halogenated hydrocarbon groups, an aromatic hydrocarbon group, and a trimethylsiloxy group;
a is equal to 1 or 2; and T is equal to (—E—U), wherein E is chosen from saturated and unsaturated, linear and branched aliphatic divalent hydrocarbon radicals having at least 2 carbon atoms and optionally containing at least one oxygen atom, or alternatively an aromatic group, and U denotes the residue of a molecule which screens ultraviolet radiation.

2. A process according to claim 1 wherein said at least one organosiloxane further comprises at least one unit chosen from units of formula (II) and units of formula (III):

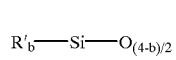
(II)

-continued

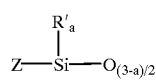
(III)

wherein:
R' and a are as defined in claim 25;
b=1, 2 or 3; and
Z =—O—U, U being defined as in claim 25.

3. A process according to claim 1 wherein at least 40% of all R' radicals in the at least one organosiloxane compound are methyl radicals.

4. A process according to claim 3 wherein at least 40% of all R' radicals in the at least one organosiloxane compound are methyl radicals and the total number of units (I), (II), and (III) present in the at least one organosiloxane compound is less than or equal to 250.

5. A process according to claim 4 wherein said total number of units (I), (II) and (III) ranges from 2 to 50.

6. A process according to claim 1 wherein U represents a residue chosen from:

benzylidenecamphor optionally substituted on the benzene ring with hydroxyl or $C_1$–$C_8$ alkyl or alkoxy radicals;

di($C_1$–$C_8$)alkyl benzalmalonate optionally substituted on the benzene ring with hydroxyl or $C_1$–$C_8$ alkyl or alkoxy radicals;

2-(2'-hydroxyphenyl)benzotriazole optionally bearing, on one of the aromatic rings, $C_1$–$C_8$ alkyl or $C_2$–$C_8$ alkenyl, halogen, alkoxy, carboxyl, hydroxyl, amino or tetraalkylpiperidyl substituents;

dibenzoylmethane optionally bearing $C_1$–$C_8$ alkyl or alkoxy or hydroxyl radicals;

benzophenone optionally bearing $C_1$–$C_8$ alkyl or alkoxy or hydroxyl radicals;

benzoate substituted with hydroxyl, $C_1$–$C_6$ alkoxy, amino or mono- or di($C_1$–$C_6$ alkyl)amino radicals;

cinnamate optionally bearing hydroxyl, $C_1$–$C_8$ alkyl or alkoxy, amino or mono- or di($C_1$–$C_6$ alkyl)amino radicals; and bis- or tris(phenylacrylate) optionally substituted with hydroxyl or $C_1$–$C_4$ alkoxy radicals.

7. A process according to claim 1 wherein said at least one organosiloxane is a benzalmalonate silicone containing at least one unit chosen from units of formula (5) and units of formula (6) below:

$$[C(O)OR'''']_2-C=CH-C_6R'''_2H_2-O-M-\underset{\underset{O_{(3-c)/2}}{|}}{\overset{\overset{R''_c}{|}}{Si}} \tag{5}$$

$$[C(O)OR'''']_2-C=CH-C_6R'''_2H_2-O-M'-\underset{\underset{O_{(3-c)/2}}{|}}{\overset{\overset{R''_c}{|}}{Si}} \tag{6}$$

wherein:
R", which may be identical or different, is chosen from an aryl and a $C_1$–$C_8$ alkyl radical;

R''', which may be identical or different, is chosen from a hydrogen, a $C_1$–$C_5$ alkyl radical and a radical OW, wherein W is chosen from hydrogen, and a $C_1$–$C_5$ alkyl radical;

R'''', which may be identical or different, denotes a $C_1$–$C_5$ alkyl group;

c is equal to 0, 1, or 2;

M is chosen from groups having the structure:

$$-\underset{\underset{(CW_2)_{\overline{n}}}{|}}{C}=CHW \quad \text{or}$$

$$-CW=CH-(CW_2)_{\overline{n}}-$$

and

M' is chosen from group having the structure:

$$-\underset{\underset{(CW_2)_{\overline{n}}}{|}}{CW}-CHW \quad \text{or}$$

$$-CW_2-CHW-(CW_2)_{\overline{n}}-$$

wherein:
W, which may be identical or different, is as defined above; and n ranges from 1 to 6;

with the proviso that the group —M—O— or —M'—O— is connected to the aromatic ring in a meta or para position relative to the group:

—CH=C—[C(O)OR""]2 and with the proviso that the two groups R''' occupy the other remaining positions on the aromatic ring;

and further wherein the other units of said benzalmalonate silicone have the structure:

$$Q_d-Si-O_{(4-d)/2} \tag{7}$$

wherein:
Q, which may be identical or different, is chosen from hydrogen, a monovalent $C_1$–$C_8$ hydrocarbon radical or a halogenated hydrocarbon group; and d is equal to 0, 1, 2, or 3.

8. A process according to claim 7 wherein said benzalmalonate silicone containing at least one unit chosen from units of formula (5) is chosen from silicones of formula (8) below:

$$V_1-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_t\left[\underset{\underset{V'_1}{|}}{\overset{\overset{CH_3}{|}}{Si}}-O\right]_u\underset{\underset{CH_3}{|}}{\overset{\overset{CH_3}{|}}{Si}}-V_1 \tag{8}$$

wherein:
V'$_1$ denotes the group having the structure:

$$HC=CH-CH_2-O-\underset{}{\underset{}{\bigcirc}}-CH=C\underset{C(O)OC_2H_5}{\overset{C(O)OC_2H_5}{\diagup}}$$

and

V$_1$, which may be identical or different, is chosen from $CH_3$ and V'$_1$;

wherein 0<t<100 and 0<u<20, with the proviso that:
when V$_1$=V'$_1$ and/or V$_2$=V'$_2$ then u=0; and
when V$_1$=$CH_3$ and/or V$_2$=$CH_3$ then 1<u<20.

9. A process according to claim 7 wherein said benzalmalonate silicone containing at least one unit chosen from units of formula (6) is chosen from silicones of formula (9) below:

$$V_2-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_t\left[\underset{\underset{V'_2}{|}}{\overset{\overset{CH_3}{|}}{Si}}-O\right]_u\underset{\underset{CH_3}{|}}{\overset{\overset{CH_3}{|}}{Si}}-V_2 \tag{9}$$

wherein:
V'$_2$ denotes the group having the structure:

$$CH_2=C-CH_2-O-\underset{}{\underset{}{\bigcirc}}-CH=C\underset{C(O)OC_2H_5}{\overset{C(O)OC_2H_5}{\diagup}}$$

and $V_2$, which may be identical or different, is chosen from $CH_3$ and $V'_2$;

wherein $0<t<100$ and $0<u<20$, with the proviso that:

when $V_1=V'_1$ and/or $V_2=V'_2$ then $u=0$; and when $V_1=CH_3$ and/or $V_2=CH_3$ then $1<u<20$.

10. A process according to claim 7 wherein said benzalmalonate silicones containing at least one unit chosen from units of each of formula (5) and formula (6) is chosen from mixtures of silicones of formula (8) and formula (9).

11. A process according to claim 1 wherein said at least one organosiloxane is present in an amount equal to at least 0.01% by weight relative to the weight of the composition.

12. A process according to claim 11 wherein said at least one organosiloxane is present in an amount ranging from 0.1 to 20% by weight relative to the weight of the composition.

13. A process according to claim 12 wherein said at least one organosiloxane is present in an amount ranging from 1 to 10% by weight relative to the weight of the composition.

14. A process according to claim 1 wherein said cosmetic or dermatological composition is in the form of an oily lotion, an alcoholic lotion, an aqueous-alcoholic lotion, an emulsion or an aqueous or aqueous-alcoholic dispersion.

15. A process according to claim 1 wherein said UV radiation is solar radiation.

16. A process according to claim 1 wherein said keratin fibers are human hair.

17. A process according to claim 1 wherein said cosmetic or dermatological composition is a hair product which is rinsed out after application.

* * * * *

UNITED STATES PATENT AND TRADEMARK OFFICE
CERTIFICATE OF CORRECTION

PATENT NO. : 6,375,940 B1
DATED : May 22, 2002
INVENTOR(S) : Hervé Richard et al.

It is certified that error appears in the above-identified patent and that said Letters Patent is hereby corrected as shown below:

<u>Title page,</u>
Item [57], ABSTRACT,
Line 2, "of,.a" should read -- of, a --.

<u>Column 12,</u>
Line 49, "claim 25" should read -- claim 1 --.
Line 51, "claim 25" should read -- claim 1 --.

<u>Column 14,</u>
Line 1, in the structure, subscript the "2".

Signed and Sealed this

Eighteenth Day of June, 2002

Attest:

*Attesting Officer*

JAMES E. ROGAN
*Director of the United States Patent and Trademark Office*